United States Patent [19]

Derible et al.

[11] 3,950,527
[45] Apr. 13, 1976

[54] N-[ω-(4'-(3''-INDOLYL)-PIPERIDINO)-ALKYL]-BENZAMIDES

[75] Inventors: Pierre Henri Derible, Le Perreux; Jacques Guillaume, Aulnay-sous-Bois; Claude Dumont, Nogent-sur-Marne, all of France

[73] Assignee: Roussel-UCLAF, Paris, France

[22] Filed: Jan. 22, 1975

[21] Appl. No.: 542,896

[30] Foreign Application Priority Data

Jan. 30, 1974 France .............................. 74.03078

[52] U.S. Cl. ............................ 424/267; 260/293.61
[51] Int. Cl.² ...................................... C07D 401/04
[58] Field of Search .............................. 260/293.61

[56] References Cited
OTHER PUBLICATIONS

Archibald, *Chem. Abst.* 1973, Vol. 79, No. 136989t.
Archibald et al., *J. Med. Chem.* 1971, Vol. 14, pp. 1054–1059.
Bruce, *Chem. Abst.* 1974, Vol. 80, No. 95560w.
Eichele et al., *Chem. Abst.* 1971, Vol. 74, No. 21674r.
Jucker et al., *Chem. Abst.*, 1969, Vol. 71, No. 81413c.
Newberry et al., *Chem. Abst.*, 1972, Vol. 77, No. 151956g.
Richter et al., *Chem. Abst.*, 1963, Vol. 58, Cols. 10134.
Tozaburo et al., *Chem. Abst.*, 1960, Vol. 54, Cols. 19576–19577.

*Primary Examiner*—Natalie Trousof
*Attorney, Agent, or Firm*—Hammond & Littell

[57] ABSTRACT

N-[ω-(4'-(3''-indolyl)-piperidino)-alkyl]-benzamides of the formula

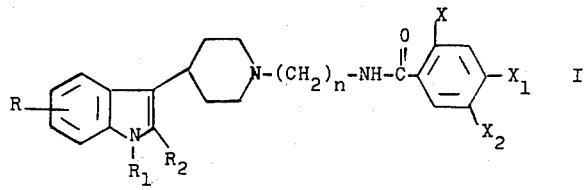

wherein R is selected from the group consisting of hydrogen and alkoxy of 1 to 3 carbon atoms, $R_1$ and $R_2$ are individually selected from the group consisting of hydrogen and alkyl of 1 to 3 carbon atoms, $n$ is 2 or 3, X is selected from the group consisting of hydrogen and alkoxy of 1 to 3 carbon atoms, $X_1$ is selected from the group consisting of hydrogen, fluorine, chlorine, bromine, —NH₂ and

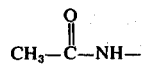

and $X_2$ is selected from the group consisting of hydrogen, chlorine and sulfamoyl and their non-toxic, pharmaceutically acceptable acid addition salts having neurosedative properties and their preparation.

17 Claims, No Drawings

N-[ω-(4'-(3''-INDOLYL)-PIPERIDINO)-ALKYL]-BENZAMIDES

STATE OF THE ART

British Pat. No. 925,429 describes 4-indolylalkyl-1-phenyl alkyl (or acyl)-piperidines having analgesic and neuroleptic activity but these compounds do not have a nitrogen atom in the chain between the phenyl and piperidinyl groups and have a carbon chain between the indolyl and piperidinyl groups.

OBJECTS OF THE INVENTION

It is an object of the present invention to provide the novel products of formula I and their non-toxic, pharmaceutically acceptable acid addition salts and their preparation.

It is another object of the invention to provide novel neurosedative compositions.

It is a further object of the invention to provide a novel method of inducing neurosedative activity in warm-blooded animals.

These and other objects and advantages of the invention will become obvious from the following detailed description.

THE INVENTION

The novel products of the invention are selected from the group consisting of benzamides of the formula

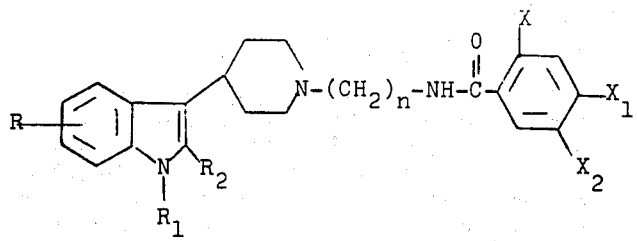

wherein R is selected from the group consisting of hydrogen and alkoxy of 1 to 3 carbon atoms, $R_1$ and $R_2$ are individually selected from the group consisting of hydrogen and alkyl of 1 to 3 carbon atoms, $n$ is 2 or 3, X is selected from the group consisting of hydrogen and alkoxy of 1 to 3 carbon atoms, $X_1$ is selected from the group consisting of hydrogen, fluorine, chlorine, bromine. —$NH_2$ and

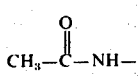

and $X_2$ is selected from the group consisting of hydrogen, chlorine and sulfamoyl and their non-toxic, pharmaceutically acceptable acid addition salts.

In the compounds of formula I, the alkoxy may be methoxy, ethoxy or propoxy or isopropoxy and the alkyl may be methyl, ethyl, propyl or isopropyl. One group of preferred compounds of formula I are those where $R_1$, X and $X_2$ are hydrogen. A more preferred group of compounds are those where $R_1$, X and $X_2$ are hydrogen, $n$ is 2 and $X_1$ is hydrogen or fluorine. Most preferred are N-/β-(4'-(3''-indolyl)-piperidino)-ethyl/-2-methoxy-4-amino-5-chlorobenzamide, N-/β-(4'-(3''-indolyl)-piperidino)-ethyl/-p-fluoro-benzamide and its acid succinate.

Examples of suitable acids for the formation of the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, maleic acid, fumaric acid, succinic acid, tartaric acid, citric acid, oxalic acid, alkanesulfonic acid, arylsulfonic acids and arylcarboxylic acids.

The novel process of the invention for the preparation of the compounds of formula I comprises reacting a compound of the formula

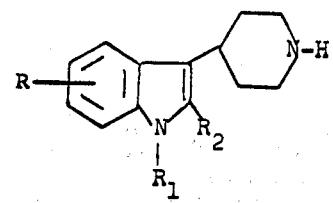

with a halide of the formula

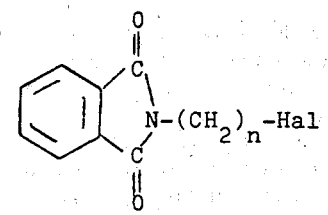

wherein R, $R_1$, $R_2$ and $n$ have the above definitions and Hal is chlorine or bromine to obtain a compound of the formula

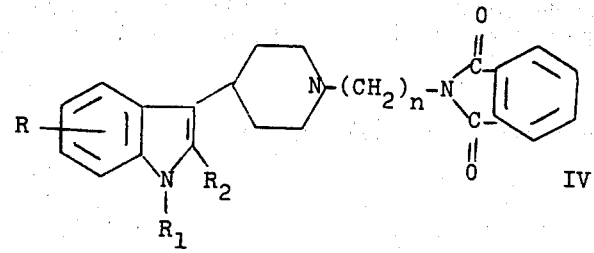

reacting the latter with hydrazine hydrate to obtain a compound of the formula

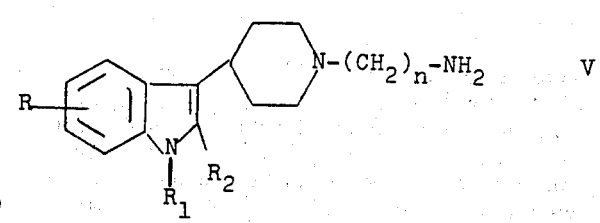

and reacting the latter with a compound of the formula

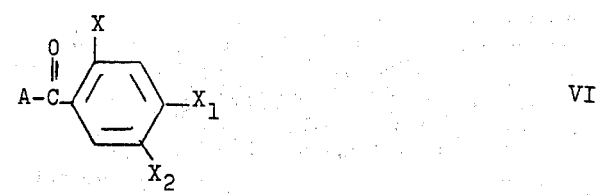

wherein A is halogen or alkoxy of 1 to 3 carbon atoms, X and $X_2$ have the above definition and $X_1$ is hydrogen, fluorine, chlorine, bromine or

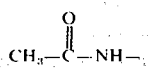

to form the corresponding compound of formula I and when $X_1$ is

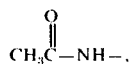

hydrolyzing the product with a mineral acid in an alkanol to obtain the corresponding compound of formula I wherein $X_1$ is $NH_2$—. The acid addition salts may be formed by reaction with the desired acid in an organic solvent.

Preferred conditions for the reaction steps of the process include effecting the initial condensation in an organic solvent such as dimethylformamide or isobutyl methyl ketone at reflux temperatures in the presence of an alkaline agent such as an alkali metal carbonate. The reaction with hydrazine is effected so as to obtain a hydrazinolysis and is effected preferably in an organic solvent such as methanol at reflux temperatures. If the compound of formula VI is the acid chloride, the reaction is preferably effected in an anhydrous organic solvent such as benzene, tetrahydrofuran or methyl ethyl ketone in the presence of a basic agent such as triethylamine or sodium carbonate. If the compound of formula VI is an alkyl ester, the reaction is preferably effected in a polyalcohol such as ethylene glycol at reflux temperatures. The hydrolysis of the acetamido group may be effected with a mineral acid such as hydrochloric acid in the presence of a lower alkanol such as ethanol.

In a variation of the process of the invention, a compound of formula V is obtained by reacting a compound of formula II with a compound of the formula

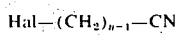

to obtain a compound of the formula

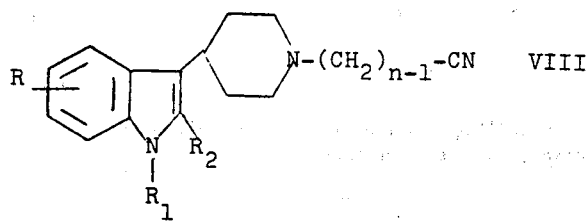

and reducing the latter to form the corresponding compound of formula V.

The preferred conditions for this modification comprises conducting the first reaction at reflux in an organic solvent such as dimethylformamide or isobutyl methyl ketone in the presence of an alkaline agent such as triethylamine or sodium carbonate and reducing the cyano with lithium aluminum hydride in an organic solvent such as ether.

The products of formula V are novel intermediates and are a part of the invention. Particularly preferred are 4-(3'-indolyl)-N-(β-aminoethyl)-piperidine, 4-(3'-indolyl)-N-(γ-aminopropyl)-piperidine and 4-(2'-methyl-6'-methoxy-3'-indolyl)-N-(β-aminoethyl)-piperidine.

The starting materials of formula II which are not known may be prepared by the process of Belgium Pat. No. 802,912 by reacting benzyl bromide and a product of the formula

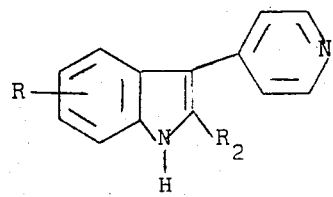

to obtain a compound of the formula

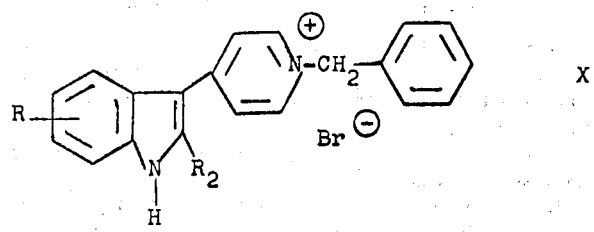

reducing the latter with sodium borohydride to obtain a compound of the formula

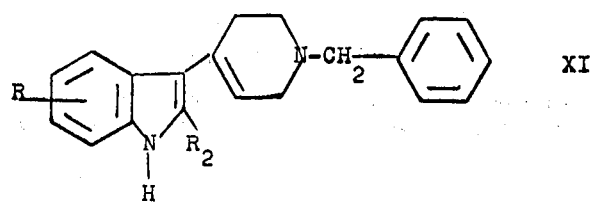

and either by reducing the compound of formula XI with hydrogen gas in the presence of palladized carbon to obtain a compound of formula II where $R_1$ is hydrogen, or by reacting a compound of formula XI with an alkyl halide where the alkyl is $R_1$ in the presence of sodium hydride to obtain a compound of the formula

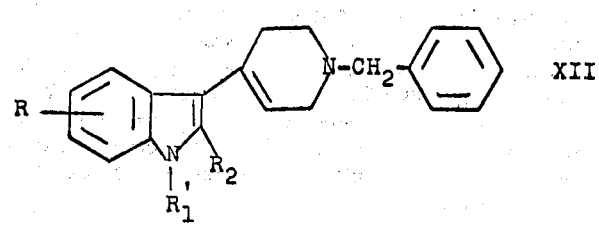

where $R_1'$ is alkyl of 1 to 3 carbon atoms and then reducing the latter with hydrogen gas in the presence of palladized carbon to obtain the corresponding compound of formula II.

The novel neurosedative compositions of the invention are comprised of an effective amount of at least one compound of formula I or its non-toxic, pharmaceutically acceptable acid addition salts and a pharmaceutical carrier. The compositions may be solids or liquids and in the form of tablets, dragees, gelules, granules, suppositories or injectable solutions or suspensions. Examples of the usual excipients are talc, arabic gum, lactose, starch, magnesium stearate, cocoa butter, aqueous or non aqueous vehicles, animal or vegetable fatty bodies, paraffinic derivatives, glycols, diverse wetting agents, dispersants or emulsifiers and preservations.

The said compositions are useful for the treatment of anxiety or hypermotivity, psychomotric agitation, irritability accompanied by insomnia and excitation states. Certain derivatives are used for treatment of character troubles, behavior troubles and certain psychoses. Certain products possess antipsychotic activity without cataleptic properties such as the acid succinate of N-[β-(4'-(3''-indolyl)-piperidino)-ethyl]-4-fluoro-benzamide.

The method of the invention for inducing neurosedative effects in humans and other warm-blooded animals comprises administering to humans or warm-blooded animals an effective amount of at least one compound of formula I or its non-toxic, pharmaceutically acceptable acid addition salts. The usual effective daily dose is .01 to 2 mg/Kg depending upon the product and the method of administration. The products may be administered orally, rectally or parenterally. The method is useful for treating anxiety, hyperemotivity, psychomotric disturbances, irritability accompanied by insomnia and excitation states.

In the following examples there are described several preferred embodiments to illustrate the invention. However, it should be understood that the invention is not intended to be limited to the specific embodiments.

EXAMPLE 1

N-[β-(4'-(3''-indolyl)-piperidino)-ethyl]-benzamide

STEP A: 4-(3'-indolyl)-N-(β-phthalimidoethyl)-piperidine

A mixture of 10 g of 3-(4'-piperidyl)-indole and 12.7 g of N-(2-bromoethyl)-phthalimide in 250 ml of isobutyl methyl ketone was heated to 80°–90°C with stirring and the 10.6 g of sodium carbonate and a few crystals of potassium iodide were added thereto. The mixture was refluxed for 2½ hours and after cooling, the mixture was added to water. The mixture was extracted with ethyl acetate and the organic phase was washed with water containing sodium chloride, was dried, concentrated to dryness. The residue was crystallized from ethyl acetate to obtain 8 g of 4-(3'-indolyl)-N-(β-phthalimido ethyl)-piperidine melting at 193°C.

STEP B: 4-(3'-indolyl)-N-(β-aminoethyl)-piperidine

A suspension of 7.21 g of the product of Step A in 72 ml of methanol and 1.93 ml of hydrazine hydrate were mixed and heated at reflux under an inert atmosphere for 45 minutes and was then cooled. 72 Ml of 2 N hydrochloric acid were added thereto and the mixture was filtered. The filtrate was made alkaline by addition of sodium hydroxide and was extracted with methylene chloride. The organic phase was washed with water containing sodium chloride, dried and concentrated to dryness to obtain 4.5 g of 4-(3'-indolyl)-N-(β-aminoethyl)-piperidine melting at 132°C.

STEP C. N-[β-(4'-(3''-indolyl)-piperidino)-ethyl]-benzamide 1.44 G of sodium carbonate were added to 3.5 g of the product of Step B in 30 ml of tetrahydrofuran cooled to 0° to 5°C and then 1.91 g of benzoyl chloride were added thereto. The temperature rose to room temperature and stirring was maintained for 15 minutes. Water was added and the precipitate formed was recovered by filtration, was washed with methylene chloride and dried. The product was crystallized from benzene to obtain 3.33 g of N-[β-(4'-(3''-indolyl)-piperidino)-ethyl]-benzamide melting at 130°C.

Analysis: $C_{22}H_{25}N_3O$. Calculated: %C, 76.05; %H, 7.25; %N, 12.09. Found: %C, 75.9; %H, 7.3; %N, 11.8.

EXAMPLE 2

N-[β-(4'-(3''-indolyl)-piperidino)-ethyl]-p-fluoro-benzamide acid succinate

A solution of 25 ml of methyl ethyl ketone and 3.6 g of p-fluorobenzoyl chloride (made from 4.9 g of p-fluorobenzoic acid and 5 g of thionyl chloride in benzene) was added at 0° to 5°C to a solution of 3.5 g of 4-(3'-indolyl)-N-(β-aminoethyl)-piperidine (Step B of Example 1) and 1.54 g of triethylamine in 25 ml of methyl ethyl ketone and the mixture was stirred for 2 hours at 20°C. The solvent was evaporated and the residue was taken up in water. The solution was made alkaline with sodium carbonate and was added to ether. The precipitate was recovered by filtration, dried and crystallized from a 1-1 benzene-cyclohexane to obtain N-[β-(4'-(3''-indolyl)-piperdine)-ethyl]-p-fluorobenzamide melting at 153°C. 1.4 g of the said product was dissolved in 100 ml of ethyl acetate and 0.5 g of succinic acid in 100 ml of ethyl acetate were added thereto. The precipitate was recovered by vacuum filtration and was crystallized from isopropanol to obtain 1 g of N-[β-(4'-(3''-indolyl)-piperidino)-ethyl]-p-fluorobenzamide succinate melting at 168°C.

Analysis: $C_{26}H_{30}FN_3O_5$. Calculated: %C, 64.58; %H, 6.25; %N, 8.69; %F, 3.93. Found: %C, 64.8; %H, 6.3; %N, 8.5; %F, 4.0.

EXAMPLE 3

N-[γ-(4'-(3''-indolyl)-piperidino)-propyl]-p-fluorobenzamide

Using the procedure of Step A of Example 1, 8 g of 3-(4'-piperidyl)-indole and 10.72 g of N-(3-bromopropyl)-phthalimide were reacted to obtain 8.9 g of 4-(3'-indolyl)-N-(γ-phthalimidopropyl)-piperidine melting at 170°C.

Using the procedure of Step B of Example 1, 8.9 g of the product of Step A and 2.4 g of hydrazine hydrate were reacted to obtain 5.44 g of 4-(3'-indolyl)-N-(γ-aminopropyl)-piperidine which melted at 96°C and was used as is for the next step.

2.5 Ml of p-fluorobenzoyl chloride were added at 0° to 5°C to a mixture of 1.8 g of sodium carbonate and 4.32 g of the above product in 45 ml of tetrahydrofuran and the mixture was added to water. The mixture was extracted with methylene chloride and the organic phase was washed with water containing sodium chloride, dried and evaporated to dryness. The raw product was purified by chromatography over silica gel and was eluted with an 85–10–5 mixture of chloroform-acetone-triethylamine to obtain a product which was crystallized from benzene to give 3.3 g of N-/γ-(4'-(3''-indolyl)-piperidino)-propyl/-p-fluorobenzamide melting at 133°C.

Analysis: $C_{23}H_{26}FN_3O$. Calculated: %C, 72.80; %H, 6.91; %F, 5.01; %N, 11.07. Found: %C, 72.7; %H, 6.8; %F, 4.8; %N, 11.2.

EXAMPLE 4

N-[β-(4'-(3''-indolyl)-piperidino)-ethyl]-p-fluoro-o-methoxy-benzamide

STEP A: 4-(3'-indolyl)-N-(cyanomethyl)-piperidine

A mixture of 20 g of 3-(4'-piperidyl)-indole, 180 ml of dimethylformamide, 10 g of triethylamine, 8.6 g of cloroacetonitrile and 20 ml of dimethylformamide was refluxed for 4 hours and the mixture was poured into a liter of cold water. The precipitate was recovered by vacuum filtration, was washed with water, dried and crystallized from 100 ml of isopropanol to obtain 14.8 g of 4-(3'-indolyl)-N-(cyanomethyl)-piperidine melting at 132°C.

STEP B: 4-(3'-indolyl)-N-(β-aminoethyl)-piperidine

A solution of 4.8 g of the product of Step A in 350 ml of ether was added dropwise to 1.9 g of lithium aluminum hydride and 50 ml of ether and the mixture was refluxed for 20 hours and then cooled. 15 Ml of ethyl acetate and then an aqueous solution of sodium potassium tartrate were slowly added to the reaction mixture. The mixture was filtered and then decanted and the ether phase was dried and evaporated to dryness. The residue was crystallized from benzene to obtain 2.8 g of 4-(3'-indolyl)-N-(β-aminoethyl)-piperidine melting at 132°C.

STEP C: N-[β-(4'-(3''-indolyl)-piperidino)-ethyl]-p-fluoro-o-methoxybenzamide 1.27 G. of sodium carbonate were added to 2.91 g of the product of Step B in 30 ml of tetrahydrofuran and after cooling to 2°C, a solution of 3.5 g of p-fluoro-o-methoxybenzoyl chloride [formed by reacting 3.06 of p-fluoro-o-methoxy-benzoic acid described in J. Chem. Soc., (1929), p. 1639 and 3 ml of thionyl chloride] in 30 ml of tetrahydrofuran was added thereto dropwise. The mixture was stirred at 0° to 2°C for 30 minutes and after the temperature returned to room temperature, the mixture was poured into water. The mixture was extracted with methylene chloride and the organic phase was washed with water containing sodium chloride, dried and concentrated to dryness. The residue was chromatographed over silica gel and eluted with an 80-15-5 mixture of chloroform-acetone-triethylamine to obtain 3.9 g of N-[β-(4'-(3''-indolyl)-piperidino)-ethyl]-p-fluoro-o-methoxy-benzamide melting at 162°C.

Analysis: $C_{23}H_{26}FN_3O_2$. Calculated: %C, 69.85; %H, 6.62; %F, 4.80; %N, 10.62. Found: %C, 69.9; %H, 6.4; %F, 4.5; %N, 10.4.

EXAMPLE 5

N-[β-(4'-(2''-methyl-6''-methoxy-3''-indolyl)-piperidino)-ethyl]-p-fluoro-benzamide STEP A: 2-methyl-6-methoxy-3-(4'-pyridyl)-indole 87 G of benzoyl chloride were added dropwise to 50 g of 2-methyl-6-methoxy-indole in 230 ml of pyridine cooled to −40°C and the mixture was stirred for 3 days in the dark at room temperature. The pyridine was evaporated under reduced pressure and the remainder was washed with aqueous sodium hydroxide and the water was evaporated. The pasty residue was dissolved in 500 ml of boiling methanol and then 200 ml of sodium hydroxide and 200 ml of water were added with stirring. The mixture was stirred for 2 hours and then allowed to stand overnight. The methanol was evaporated under reduced pressure and the aqueous phase was extracted with chloroform. The organic phase was dried over sodium sulfate and evaporated under reduced pressure to obtain 100 g of raw product which was chromatographed over alumina and eluted with benzene to obtain 34 g of a product in the form of brown crystals. The product was crystallized from acetonitrile to obtain 19.5 g of 2-methyl-6-methoxy-3-(4'-pyridyl)-indole melting at 196°–198°C.

STEP B: 1-benzyl-4-(6'-methoxy-2'-methyl-3'-indolyl)-pyridine-bromide

A mixture of 3.4 g of 2-methyl-6-methoxy-3-(4'-pyridyl)-indole and 2.65 g of benzyl bromide in 30 ml of ethylacetate was refluxed for 4 hours and after cooling the mixture was vacuum filtered. The yellow crystals were washed with ethyl acetate and dried to obtain 5.7 g of 1-benzyl-4-(6'-methoxy-2'-methyl-3' -indolyl)-pyridinium bromide melting at 244°–246°C.

STEP C: 3-(1'-benzyl-1',2',3',6'-tetrahydro-4'-pyridyl)-6-methoxy-2-methyl-indole 1 g of 1-benzyl-4-(6'-methoxy-2'-methyl-3'-indolyl)-pyridinium bromide was added at 35°–40°C to 165 ml of methanol and 70 ml of water and after cooling the mixture to 25°C, 4 g of sodium borohydride were added thereto in small portions at a temperature not greater than 30°–35°C. The mixture was stirred for 2 hours at room temperature and was then poured into water. The precipitate was vacuum filtered and was washed with water and dried under reduced pressure to obtain 15.4 g of 3-(1'-benzyl-1',2',3',6'-tetrahydro-4'-pyridyl)-6-methoxy-2-methyl-indole melting at 142°–143°C.

STEP D: 6-methoxy-2-methyl-3-(4'-piperidyl)-indole

A mixture of 24 g of 3-(1'-benzyl-1',2',3',6'-tetrahydro-4'-pyridyl)-6-methoxy-2-methyl-indole, 4 g of carbon containing 10% palladium and 300 ml of absolute ethanol was heated to 50°C and hydrogen was introduced and after 12 hours, 2450 ml of hydrogen were absorbed. The catalyst was filtered off and another 3.0 g of 10% palladized carbon were added while continuing the hydrogen flow. The hydrogenation continued for 3½ hours during which 3250 ml of hydrogen were absorbed. The catalyst was filtered and the ethanol was evaporated under reduced pressure to obtain 16.6 g of 6-methoxy-2-methyl-3-(4'-piperidyl)-indole melting at 166°C.

STEP E: 4-(2'-methyl-6'-methoxy-3'-indolyl)-N-(β-phthalimido ethyl)-piperidine

Using the procedure of Step A of Example 1, 12.21 g of 2-methyl-3-(4'-piperidyl)-6-methoxy-indole and 15 g of N-(2-bromoethyl)-phthalimide were reacted to obtain a raw product which was chromatographed over silica gel and eluted with a 97-3 ethyl acetate-triethylamine mixture to obtain 11.15 g of amorphous 4-(2'-methyl-6'-methoxy-3'-indolyl)-N-(β-phthalimidoethyl)-piperidine.

IR Spectrum (chloroform): Presence of NH at $3459^{cm-1}$, C=O at 1778 and $1713^{cm-1}$, C=C and aromatic.

STEP F: 4-(2'-methyl-6'-methoxy-3'-indolyl)-N-(β-aminoethyl)-piperidine

Using the procedure of Step B of Example 1, 11.15 g of the product of Step A and 2.67 g of hydrazine hydrate were reacted to obtain 6.85 g of amorphous 4-(2'-methyl-6'-methoxy-3'-indolyl)-N-(β-aminoethyl)-piperidine.

IR Spectrum (chloroform): Presence of $NH_2$ at $3378^{cm-1}$, NH and aromatic.

STEP G: N-[β-(4'-(2''-methyl-6''-methoxy-3''-indolyl)-piperidino)-ethyl]-p-fluorobenzamide Using the procedure of Step C of Example 1, 6.85 g of the product of Step B, 2.43 g of sodium carbonate and 5.5 g of p-fluorobenzoyl chloride were reacted and the raw product was extracted with methylene chloride and chromatographed over silica gel and elution with a 60-30-10 mixture of chloroform-acetone-triethylamine to obtain, after crystallization from benzene, 3.2 g of N-[β-(4'-(2''-methyl-6''-methoxy-3''-indolyl)-piperidino)-ethyl]-p-fluoro-benzamide melting at 170°C.

Analysis: $C_{24}H_{28}FN_3O_2$. Calculated: %C, 70.39; %H, 6.89; %F, 4.63; %N, 10.26. Found: %C, 70.6; %H, 6.9; ; %F, 4.3; %N, 10.2.

EXAMPLE 6

N-[β-(4'-(3''-indolyl)-piperidino)-ethyl]-2-methoxy-4-acetamido-5-chloro-benzamide A solution of 5.2 g of 2-methoxy-4-acetamide-5-chloro-benzoyl chloride in 450 ml of benzene was slowly added at 10° to 15°C to a mixture of 4.9 g of 4-(3'-indolyl)-N-(β-aminoethyl)-piperidine and 2.1 g of triethylamine in 350 ml of benzene and the mixture was stirred for 18 hours and then was poured into water. The mixture was extracted with methylene chloride and the organic phase was washed with water, dried and concentrated to dryness. The residue was crystallized from methyl ethyl ketone to obtain 8 g of N-[β-(4'-(3''-indolyl)-piperidino)-ethyl]-2-methoxy-4-acetamido-5-chloro-benzamide melting at 208°C.

Analysis: $C_{25}H_{29}ClN_4O_3$. Calculated: %C, 64.02, %H, 6.23; %N, 11.95; %Cl, 7.51. Found: %C, 63.8; %H, 6.4; %N, 11.8; %Cl, 7.6.

EXAMPLE 7

N-[β-(4'-(3''-indoyl)-piperidino)-ethyl]-2-methoxy-4-amino-5-chloro-benzamide 400 ml of an 8 N hydrochloric acid solution in ethanol were added to a suspension of 8 g of the product of Example 6 in 50 ml of ethanol and the mixture was refluxed for 30 minutes and then was cooled. The mixture was held at 20°C for 1 hour and then was concentrated to dryness to obtain the dihydrochloride of N-[β-(4'-(3''-indolyl)-piperidino)-ethyl]-2-methoxy-4-amino-5-chloro-benzamide. The product was crystallized from acetone and then was taken up in a mixture of methylene chloride — 2 N sodium hydroxide. The organic phase was dried and concentrated to dryness and the residue was crystallized from ethanol to obtain 1.8 g of the free base melting at 208°C.

Analysis: $C_{23}H_{27}ClN_4O_2$. Calculated: %C, 64.70; %H, 6.38; %N, 13.12; %Cl, 8.30. Found: %C, 64.4; %H, 6.3; %N, 12.9; %Cl, 8.3.

EXAMPLE 8

N-[β-(4'-(3''-indolyl)-piperidino)-ethyl]-2-methoxy-5-sulfamoyl-benzamide 2.4 G of methyl 2-methoxy-5-sulfamoyl-benzoate [described in Acta Chim. (Budapest), Vol. 69 1 (1971), p. 81–86] were added slowly at 140°C to a solution of 5 g of 4-(3'-indolyl)-N-(β-aminoethyl)-piperidine in 50 ml of ethylene glycol and after cooling the mixture, 50 ml of methanol were added thereto. The crystals formed were vacuum filtered and dissolved in hot dimethylformamide and crystallized by addition of acetonitrile to the solution to obtain 2.09 g of N-[β-(4'-(3''-indolyl)-piperidino)-ethyl]-2-methoxy-5-sulfamoyl-benzamide melting at 283°C.

Analysis: $C_{23}H_{28}N_4O_4S$ Calculated: %C, 60.51; %H, 6.18; %N, 12.27; %S, 7.02. Found: %C, 60.3; %H, 6.3; %N, 12.2; %S, 6.8.

EXAMPLE 9

Tablets were prepared from 10 mg of the acid succinate of N-[β-(4'-(3''-indolyl)-piperidino)-ethyl]-p-fluorobenzamide or N-[β-(4'-(3''-indolyl)-piperidino)-ethyl]-2-methoxy-4-amino-5-chloro-benzamie and sufficient excipient of lactose, starch, talc and magnesium stearate. An injectable solution was prepared from 10 mg of acid succinate of N-[β-(4'-(3''-indolyl)-piperidino)-ethyl]-p-fluoro-benzamide and sufficient distilled water to form a solution of 2 ml.

PHARMACOLOGICAL STUDY

Neurosedative Activity

A. Traction Test

This test consisted of suspending a mouse by the front paws from a horizontal metal wire and in a time of less than 5 seconds, the normal mouse will effect a reestablishment by managing to place at least one hind paw on the wire. The test was effected 30 minutes after intraperitoneal administration of the test compound and the $DE_{50}$ dose, that dose at which 50 % of the animals do not reestablished themselves in 5 seconds, was determined. The results are in Table I.

B. Chimney Test

This test consisted of placing a mouse in the end of a glass tube 30 cm long with a diameter adapted to the size of the mouse. The tube was straightened vertically in a rapid manner with the head of the mouse at the base. The normal uprighting time for the mouse in the tube was less than 30 seconds. The test was conducted 30 minutes after intraperitoneal administration of the test product and the $DE_{50}$ dose was determined and is reported in Table I.

C. Antagonism to toxicity of amphetaminic compounds

This test was determined on groups of 10 male mice in a crystallizer with a 20 cm diameter and a 9 cm height covered with a grill. The animals received an intraperitoneal injection of 15 mg/kg of dexamphetamine sulfate 30 minutes after intraperitoneal administration of the test product. The group mortality was counted 24 hours after the injection of dexamphetamine sulfate and the $DE_{50}$ dose was determined. The results are in Table I.

TABLE I

| Product of Example | $DE_{50}$ in mg/kg | | Antagonism to toxicity of amphetamines |
|---|---|---|---|
| | Traction Test | Chimney Test | |
| 1 | 18 | 7 | 3 |
| 2 | 6.5 | 2 | 0.3 |
| 3 | 20 | 5 | 8 |
| 4 | 8.5 | 4.5 | 0.35 |
| 5 | 25 | 17 | 3 |

The results of Table I show that the test products possess important neurosedative properties.

In the following tests, the product of Example 2, acid succinate of N-[β-(4'-(3''-indolyl)-piperidino)-ethyl]-p-fluoro-benzamide, was subjected to tests which demonstrate that it has an important antipsychotic activity and is practically devoid of cataleptigenic activity.

A. Antagonism to stereotypes provoked by amphetamine

This test consisted of using groups of 5 rats which were placed in individual grill cages. The rats received intraperitoneally 8 mg/kg of dexamphetamine sulfate 30 minutes after intraperitoneal administration of the test products and the test used controls and treated animals. The rating scale was that described by Halliwel et al. [Brit. J. Pharmacol., Vol. 23 (1964), p. 330–350] and the $DE_{50}$ of the product was 17.5 g mg/kg.

B. Antagonism to sterotypes provoked by apomorphine

This test used groups of 5 male rats in a test inspired by Janssen et al. [Arzn. Forsch., Vol. 15 (1965), p. 104–117 and Vol. 17 (1967), p. 841–854] with each rat in an individual grill cage. Each animal received an intravenous injection in the vein of the penis of 1.5 mg of apomorphine hydrochloride 30 minutes after intraperitoneal administration of the test compound. The animals, control and treated, were observed 1,5,10 and 15 minutes after the last injection and the stereotype movements of the buccal sphere were evaluated for their intensity on a scale of 0 to 3 as by Boissier et al. [Therapie., Vol. 25 (1970), p. 939–949]. The height of the test was determined and the $DE_{50}$ dose was ascertained to be 10 mg/kg.

C. Antagonism to vomitting provoked by apomorphine

This test was effected on dogs as reported by Chen et al. [*J. Pharmac. exp. Therap.* Vol. 93 (1950), p. 245–250]. The test product was subcutaneously administered 30 minutes before subcutaneous administration of 0.1 mg/kg of apomorphine hydrochloride. The number of vomitting was observed in one half hour after the apomorphine administration. The cross tests were repeated after 8 days on lots of 2 dogs and the $DE_{50}$ dose was determined to be 0.005 mg/kg.

D. Cataleptic Power

This test is described by Boissier et al. [*Therapie.*, Vol. 18 (1963), p. 1257–1277] and was effected on young rats by crossing the homolateral paws and noting the intensity of catalepsy. The test product was intraperitoneally administered and the $DE_{50}$ was formed to be greater than 60 mg/kg.

Acute toxicity

The acute toxicity was determined by intraperitoneal administration of the test compounds to mice in increasing doses and determination of the mortality after 48 hours to determine the $DL_{50}$ dose. The results are in Table II.

TABLE II

| Product of Example | $DL_{50}$ in mg/kg |
|---|---|
| 1 | 300 |
| 2 | 125 |
| 3 | 60 |
| 4 | >800 |
| 5 | 400 |
| 7 | >800 |
| 8 | 800 |

Various modifications of the products and methods of the invention may be made without departing from the spirit or scope thereof and it is to be understood that the invention is to be limited only as defined in the appended claims.

We claim:

1. A compound selected from the group consisting of benzamides of the formula

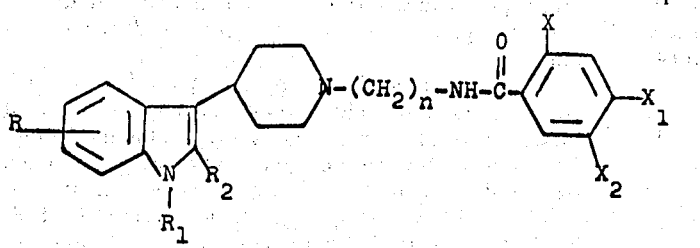

wherein R is selected from the group consisting of hydrogen and alkoxy of 1 to 3 carbon atoms, $R_1$ and $R_2$ are individually selected from the group consisting of hydrogen and alkyl of 1 to 3 carbon atoms, n is 2 or 3, X is selected from the group consisting of hydrogen and alkoxy of 1 to 3 carbon atoms, $X_1$ is selected from the group consisting of hydrogen, fluorine, chlorine, bromine, $-NH_2$ and

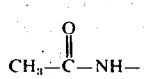

and $X_2$ is selected from the group consisting of hydrogen, chlorine and sulfamoyl and their non-toxic, pharmaceutically acceptable acid addition salts.

2. A compound of claim 1 wherein $R_1$, X and $X_2$ are hydrogen.

3. A compound of claim 2 wherein n is 2 and $X_1$ is selected from the group consisting of hydrogen and fluorine.

4. A compound of claim 1 selected from the group consisting of N-[β-(4'-(3''-indolyl)-piperidino)-ethyl]-benzamide and its non-toxic, pharmaceutically acceptable acid addition salts.

5. A compound of claim 1 selected from the group consisting of N-[β-(4'-(3''-indolyl)-piperidino)-ethyl]-p-fluoro-benzamide and its non-toxic, pharmaceutically acceptable acid addition salts.

6. A compound of claim 1 selected from the group consisting of N-[γ-(4'-(3''-indolyl)-piperidino)-propyl]-p-fluoro-benzamide and its non-toxic, pharmaceutically acceptable acid addition salts.

7. A compound of claim 1 selected from the group consisting of N-[β-(4'-(3''-indolyl)-piperidino)-ethyl]-p-fluoro-o-methoxy-benzamide and its non-toxic, pharmaceutically acceptable acid addition salts.

8. A compound of claim 1 selected from the group consisting of N-[β-(4'-(2''-methyl-6''-methoxy-3''-indolyl)-piperidino)-ethyl]-p-fluoro-benzamide and its non-toxic, pharmaceutically acceptable acid addition salts.

9. A compound of claim 1 selected from the group consisting of N-[β-(4'-(3''-indolyl)-piperidino)-ethyl]-2-methoxy-4-acetamido-5-chloro-benzamide and its non-toxic, pharmaceutically acceptable acid addition salts.

10. A compound of claim 1 selected from the group consisting of N-[β-(4'-(3''-indolyl)-piperidino)-ethyl]-2-methoxy-4-amino-5-chloro-benzamide and its non-toxic, pharmaceutically acceptable acid addition salts.

11. A compound of claim 1 selected from the group consisting of N-[β-(4'-(3''-indolyl)-piperidino)-ethyl]-2-methoxy-5-sulfamoyl-benzamide and its non-toxic, pharmaceutically acceptable acid addition salts.

12. A neurosedative composition comprising an effective amount of at least one compound of claim 1 and a pharmaceutical carrier.

13. A composition of claim 10 wherein $R_1$, X and $X_2$ are hydrogen.

14. A method of inducing neurosedative activity in humans or warm-blooded animals comprising administering to humans or warm-blooded animals a neurosedatively effective amount of at least one compound of claim 1.

15. The method of claim 14 wherein $R_1$, X and $X_2$ are hydrogen.

16. The method of claim 14 wherein the compound is N-[β-(4'-(3''-indolyl)-piperidino)-ethyl]-2-methoxy-4-amino-5-chloro-benzamide.

17. The method of claim 14 wherein the compound is the acid succinate of N-[β-(4'-(3''-indolyl)-piperidino)-ethyl]-p-fluoro-benzamide.

* * * * *

UNITED STATES PATENT OFFICE
CERTIFICATE OF CORRECTION

Patent No. 3,950,527   Dated April 13, 1976

Inventor(s) PIERRE HENRI DERIBLE, JACQUES GUILLAUME and CLAUDE DUMONT

It is certified that error appears in the above-identified patent and that said Letters Patent are hereby corrected as shown below:

| Col. | Line | |
|---|---|---|
| 1 | 14 | Please delete the word "present" |
| 5 | 44 | "72 Ml" should be --72 ml-- |
| 6 | 39 | "2.5Ml" should be --2.5 ml-- |
| 6 | 63 | "cloroacetonitrile" should be --chloroacetonitrile-- |
| 7 | 3 | "15Ml" should be --15 ml-- |
| 7 | 14 | "1.27G" should be --1.27 g-- |
| 7 | 17 | "3.06" should be --3.06 g-- |
| 7 | 41 | "87G" should be --87 g-- |
| 9 | 38 | "2.4G" should be --2.4 g-- |
| Claims | | |
| 12 | 55 | "Claim 10" should be --claim 12-- |

Signed and Sealed this

Twenty-first Day of September 1976

[SEAL]

Attest:

RUTH C. MASON
*Attesting Officer*

C. MARSHALL DANN
*Commissioner of Patents and Trademarks*